United States Patent [19]
Ozasa

[11] Patent Number: 5,334,146
[45] Date of Patent: Aug. 2, 1994

[54] CATHETER BALLOON HAVING VARYING WALL THICKNESS

[75] Inventor: Hitoshi Ozasa, Nakai, Japan

[73] Assignee: Terumo Kabushiki Kaisha, Tokyo, Japan

[21] Appl. No.: 790,637

[22] Filed: Nov. 8, 1991

[30] Foreign Application Priority Data

Nov. 10, 1990 [JP] Japan .................. 2-304559

[51] Int. Cl.$^5$ ........................................... A61M 29/00
[52] U.S. Cl. ...................................... 604/96; 604/194
[58] Field of Search .................. 604/96, 99, 101, 103; 606/192, 194, 195

[56] References Cited

U.S. PATENT DOCUMENTS

| | | | |
|---|---|---|---|
| 2,610,626 | 9/1952 | Edwards | 604/96 |
| 4,490,421 | 12/1984 | Levy . | |
| 4,906,244 | 3/1990 | Pinchuk et al. . | |
| 4,932,956 | 6/1990 | Reddy et al. | 606/192 |
| 4,943,278 | 7/1990 | Euteneuer et al. | 604/96 |
| 4,963,313 | 10/1990 | Noddin et al. | 604/96 |

FOREIGN PATENT DOCUMENTS

| | | |
|---|---|---|
| 0274411 | 7/1988 | European Pat. Off. . |
| 0318919 | 6/1989 | European Pat. Off. . |
| 0362826 | 4/1990 | European Pat. Off. . |
| 63-26655 | 5/1988 | Japan . |
| 63-183070 | 7/1988 | Japan . |
| WO89/07958 | 9/1989 | World Int. Prop. O. . |

*Primary Examiner*—John D. Yasko
*Assistant Examiner*—Anthony Gutowski
*Attorney, Agent, or Firm*—Frishauf, Holtz, Goodman & Woodward

[57] ABSTRACT

A catheter balloon made of a polymer and comprising a cylindrical portion of a substantially uniform diameter, tapered portions at the front and rear of the cylindrical portion and connecting portions at the front and rear of the tapered portions, wherein the wall thicknesses (B) of the middle parts of the tapered portions are equal to or smaller than 1.2 times the wall thickness (A) of the cylindrical portion (B/A $\leq$ 1.2), and the wall thickness of the front tapered portion is less than the wall thickness of the rear tapered portion.

6 Claims, 5 Drawing Sheets

CATHETER BALLOON HAVING VARYING WALL THICKNESS

BACKGROUND OF THE INVENTION

The present invention relates to a balloon used for various kinds of balloon catheters, especially for a dilatation catheter used for expanding a stenotic lesion in a blood vessel, a catheter equipped with the balloon, and the method or manufacturing the balloon.

There are proposed some methods of manufacturing a balloon for a catheter balloon. Disclosed in Japanese Patent Provisional Publication gazette No. 26655/1988, for example, is a method of manufacturing a biaxially-drawn polymer balloon, in which a thin wall tubular parison is formed out of a drawable hemicrystalline polymer, the parison is stretched out in the direction of its length and then inflated radially at a temperature in the range from the second-order transition temperature to the first-order transition temperature, and the thus-drawn parison is cooled below the second-order transition temperature and deflated.

Another method of manufacturing a biaxially-drawn polymer balloon is proposed in Japanese Patent Provisional Publication gazette No. 183070/1988, in which the parison drawn by the same method is heated to a temperature above the drawing temperature while drawn to raise the crystallinity and then cooled below the second-order transition temperature.

The catheter balloon manufactured by the above conventional methods consists of a cylindrical portion of a substantially uniform diameter, tapered portions at the front and rear of the cylindrical portion, and thinner cylindrical connecting portions at the front and rear of the tapered portions.

The wall thickness of the catheter balloon made by the above methods is not uniform and the walls of both tapered portions are thicker than that of the cylindrical portion. More specifically the wall thicknesses b1 and b2 of the middle parts of the tapered portions are thicker than the thickness a of the cylindrical portion as shown in FIG. 4. Here the middle part of the tapered portions 3a and 3b means the vicinity of the middle point of their length along the axis of the balloon 1. Because of their thicker walls, the tapered portions wrinkle when the balloon is folded and the wrinkles are angular, protuberant and stiff. These wrinkles can hinder the smooth insertion of the balloon into a stenotic lesion in the blood vessel or hurt the inside surface of the blood vessel to cause thrombosis or stenosis.

SUMMARY OF THE INVENTION

The present invention provides an improved catheter balloon, the protruberation and angularness of the tapered portions of which when folded are small and soft, and which can be inserted into a blood vessel without hurting the inside surface of the blood vessel and which can be easily passed through a stenotic lesion.

The present invention also provides a balloon catheter using the balloon of the present invention and a method of manufacturing the balloon of the present invention.

The catheter balloon of the present invention is made of a polymer, comprises a cylindrical portion of a substantially uniform diameter, tapered portions at the front and rear of the cylindrical portion and connecting portions at the front and rear of the tapered portions, and is characterized in that the wall thicknesses (B) of the substantially middle parts of the tapered portions are equal to or smaller than 1.2 times the wall thickness (A) of the cylindrical portion (B/A $\leq$ 1.2).

The balloon catheter of the present invention comprises a tubular catheter body and a balloon, the balloon made of a polymer and comprising a cylindrical portion of a substantially uniform diameter, tapered portions at the front and rear of the cylindrical portion and connecting portions at the front and rear of the tapered portions and characterized by that the wall thicknesses (B) of the substantially middle parts of the tapered portions are equal to or smaller than 1.2 times the wall thickness (A) of the cylindrical portion (B/A $\leq$ 1.2).

The method of the present invention of manufacturing a balloon catheter comprises forming a tubular parison made of a drawable polymer, heating the parison at a temperature in the range from the second-order transition temperature to the first-order transition temperature of the polymer used, and then stretching it in the direction of its axis and then inflating it radially while heated, end then cooling the stretched and inflated parison below the second-order transition temperature of the polymer, end then deflating it, a crude balloon thus formed having a cylindrical portion of a substantially uniform desired diameter and desired wall thickness, tapered portions of the wall thicknesses thicker than desired thicknesses at the front and rear of the cylindrical portion and connecting portions at the front and the rear of the tapered portions, and then redrawing the tapered portions of the crude balloon to reduce their wall thicknesses to desired thicknesses by stretching the tapered portions in the direction of the axis of the crude balloon,

DETAILED DESCRIPTION OF THE PREFERRED EMBODIMENTS

The catheter balloon of the present invention described below by the embodiment shown in the figures.

Figure 1:
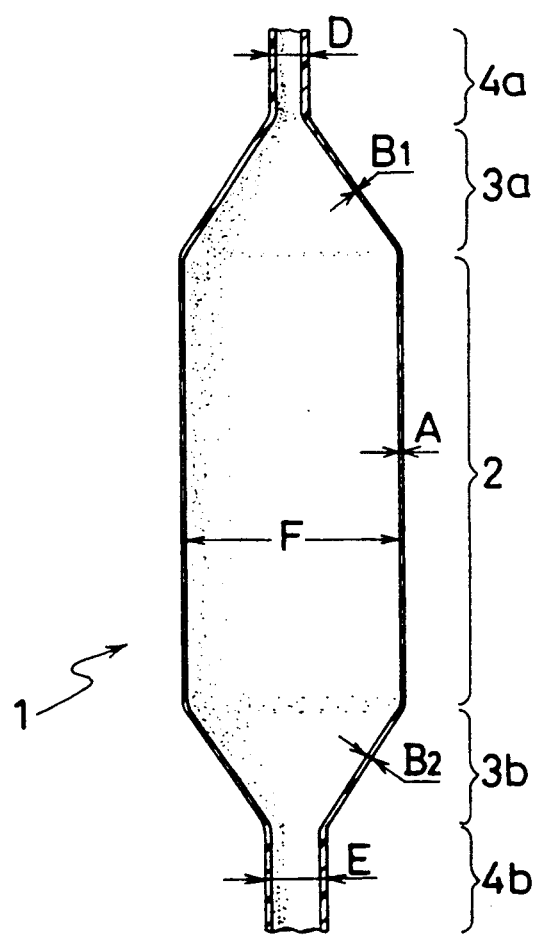
FIG. 1 is a sectional view of an embodiment of the catheter balloon of the present invention.

FIG. 1 is a sectional view of an embodiment of the catheter balloon of the present invention.

A catheter balloon of the present invention is made a polymer, comprises a cylindrical portion 2 of a substantially uniform diameter, tapered portions 3a and 3b at the front and rear of the cylindrical portion and tubular connecting portions 4a and 4b at the front and rear of the tapered portions, and is characterized in that the wall thicknesses (B) of the substantially middle parts of the tapered portions are equal to or smaller than 1.2 times the wall thickness (A) of the cylindrical portion (B/A≦1.2). Since the walls of the tapered portions are thin, the protruberation and angulateness of wrinkles caused by the tapered portions when the balloon is folded are smaller and softer than those of conventional balloons. Therefore, the balloon of the present invention, when used in a dilatation catheter, can be inserted easily in the blood vessel without hurting the inside surface of the blood vessel and thereby causing new thrombosis or stenosis.

This balloon 1 is intended to be used with a dilatation catheter. The balloon 1 is made of a polymer and foldable. It is folded around the tubular catheter body when the balloon is deflated. The balloon 1 comprises a cylindrical portion 2, tapered portions 3a and 3b, and connecting portions 4a and 4b.

The cylindrical portion 2 has a largest, substantially uniform diameter over its length. The cylindrical portion 2 need not a right cylinder, but may be a polygonal prism.

The tapered portions 3a and 3b extend from the front and rear ends of the cylindrical portion 2 respectively and become gradually smaller in diameter.

The connecting portions 4a and 4b extend respectively from the front and rear tapered portions 3a and 3b and have a cylindrical configuration of a substantially uniform diameter smaller than that of the cylindrical portion 2. The balloon 1 is attached to a catheter body by the connecting portions 4a and 4b.

The tapered portions 3a and 3b and the connecting portions 4a and 4b may be different from each other in their configuration and diameter as shown in FIG. 1.

The outside diameter of the cylindrical portion 2 when the balloon is expanded is 1.0 to 35.0 mm, preferably 1.5 to 35.0 mm, the length of the cylindrical portion 2 is 3.0 to 80.0 mm, preferably 10.0 to 75.0 mm, and the overall length of the balloon is 5.0 to 120.0 mm, preferably 15.0 to 100.0 mm.

As shown in FIG. 1, the wall thickness A of the cylindrical portion 2 and those indicated by B1 and B2 of the substantially middle parts of the tapered portions 3a and 3b are formed so as to be B1/A≦1.2, preferably 0.3≦B1/A≦0.9 or B1/A≦1.2 and B2/A≦1.2, preferably 0.3≦B1/A≦0.9 and 0.3≦B2/A≦0.9.

If B1/A (and B2/A) is equal to or smaller than 0.9, the protruberation and angulateness of the tapered portions 3a and 3b when the balloon is folded are small and soft. If B1/A (and B2/A) is equal to or greater than 0.3, the walls of the tapered portions 3a and 3b have an adequate strength. It is preferable that the wall thickness B1 of the front tapered potion 3a is thinner than the wall thickness B2 of the rear tapered potion 3b (B1<B2).

It is preferable that the balloon 1 is drawn biaxially. For this purpose, the balloon 1 is drawn both in the direction of its axis and in the direction perpendicular to its axis. By thus drawing biaxially, the wall thickness of the balloon 1 becomes thinner end the strength of the balloon 1 increases.

It is further preferable that the tapered portions 3a and 3b are redrawn. By redrawing the tapered portions 3a and 3b, their wall thickness can be made thinner as desired.

Polymers usable for the balloon of the present invention are, for example, polyethylene terephthalate, a polyester (ethylene terephthalate copolymer) obtained from a principal acid or a principal glycol, a mixture of polyethylene terephthalate and a polyester other than polyethylene terephthalate, a mixture of polyethylene terephthalate and polyolefin (for example, polyethylene and polypropylene), or polyethylene terephthalate copolymer.

The polyesters usable for the balloon of the present invention are those obtained using isophthalic acid, orthophthalic acid, naphthalene dicarboxylic acid, paraphenylene dicarboxylic acid, cyclohexane dicarboxylic acid, succinic acid, gluteric acid, adipic acid, suberic acid, azelaic acid, sebacic acid, dodecane-dionic acid, trimellitic acid, pyromellitic acid, sulfoisophthalic acid and their salt for the principal acid and using polypropylene glycol, butanediol, pentanediol, hexanediol, neopentyle glycol, diethylene glycol, triethylene glycol, polyethylene glycol, polytetramethylene glycol, cyclohexane dimethanol, ethylene oxide-added bisphenol A, trimethylol propane, pentaerythritol for the principal glycol.

Next the method of the present invention for manufacturing the catheter balloon of the present invention is described.

In this method, first a tubular parison is formed of a drawable or orientable polymer. Next the parison is heated at a temperature in the range from the second-order transition temperature to the first-order transition temperature of the polymer use. The heated parison is stretched in the direction of its axis and then inflated radially. While stretched and inflated, the parison is cooled below the second-order transition temperature of the polymer and deflated. Thus obtained is a partially shaped or crude balloon. Next the tapered portions of the crude balloon are redrawn by stretching to reduce their wall thickness. The balloon is inflated again and heated above the second transition temperature of the polymer. The balloon is cooled while inflated and deflated.

Each step of the above process is described below in detail.

Figure 2:
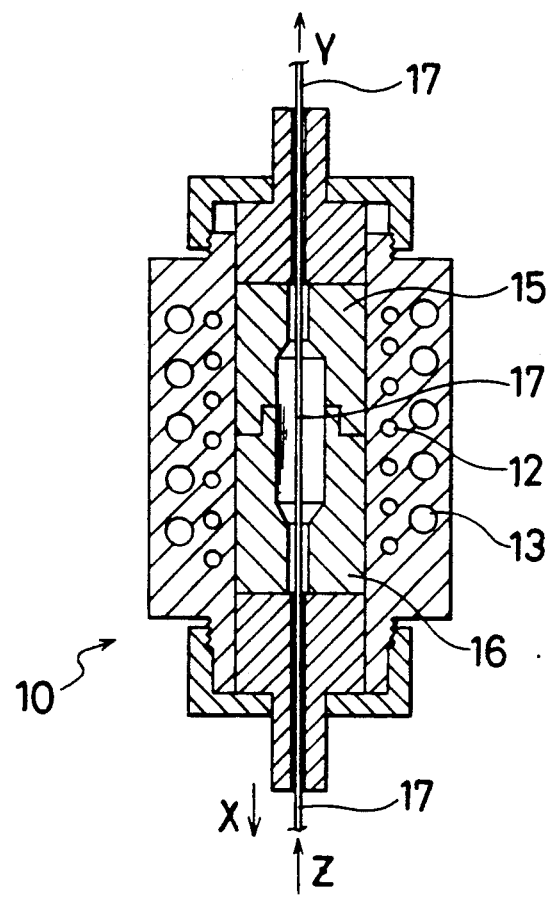
FIG. 2 is a sectional view of the metal mold for forming the balloon of the present invention.

First, a tubular parison 17 as shown in FIG. 2 is formed of a drawable polymer. The polymers described above can be used for the material.

Next, the tube 17 is put into a metal mold 10 as shown in FIG. 2 and one end of the tube 17 is clamped in an airtight fission (not shown). The clamping is made by melting by heat or by means of a forceps. FIG. 2 is a sectional view of e metal mold 10 for forming the balloon. The metal mold 10 is provided with a heating coil 12 and a cooling conduit 13. The metal molded 10 comprises divided metal molds 15 and 16 the inside surfaces of which form the external shape of the crude balloon when the metal molds 15 and 16 are Combined.

Figure 4:
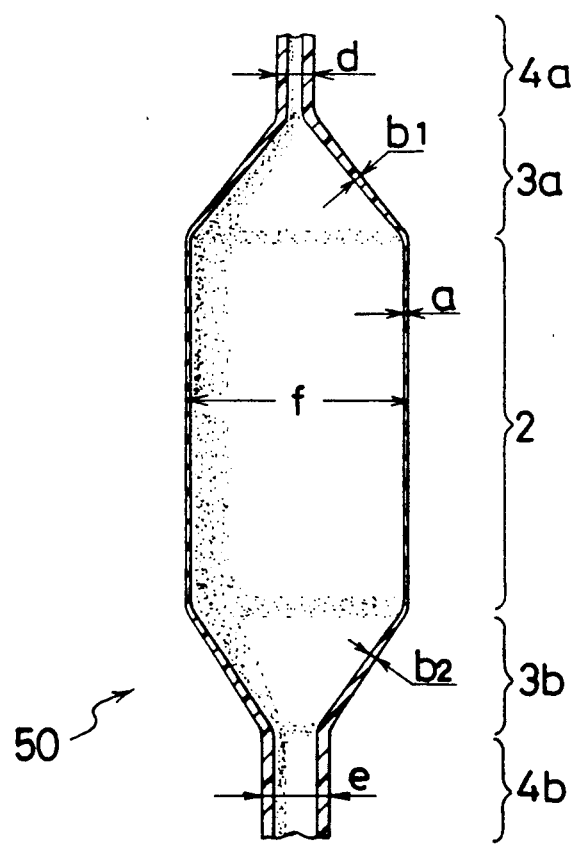
FIG. 4 is a sectional view of the partially formed crude balloon before redrawn.

As shown in FIG. 2, the tube 17 is then heated to a temperature in the range from the second-order transition temperature to the first-order transition temperature of the polymer used, more specifically a temperature a little higher than the second-order transition temperature, by turning on the heater 12. While being heated, the tube 17 is stretched along its axis by pulling it in the directions indicated by arrows X and Y, then inflated by introducing air under pressure in the direction indicated by Z so that the heated part of the tube 17 is tightly pressed against the inside surfaces of the metal molds 15 end 16. While inflated, the tube 17 is cooled below the second-order transition temperature of the polymer by flowing a cooling liquid in the cooling conduit 13. The tube 17 may be cooled by free cooling without using a cooling liquid. After the tube 17 has cooled, the air in the tube 17 is released and the tube 17 is taken out from the metal mold 10. Then the front and rear end portions of the tube 17 are cut off and a biaxially-drawn or biaxially-oriented crude balloon as shown in FIG. 4 is obtained. The crude balloon has a cylindrical portion of s substantially uniform desired diameter and desired wall thickness, tapered portions of the wall thickness thicker than a desired thickness at the front and rear of the cylindrical portion end connecting portions at the front and the rear of the tapered portions. This drawing process may be repeated two or more times as necessary to obtain a crude baloon with a desired wall thickness.

Figure 3:
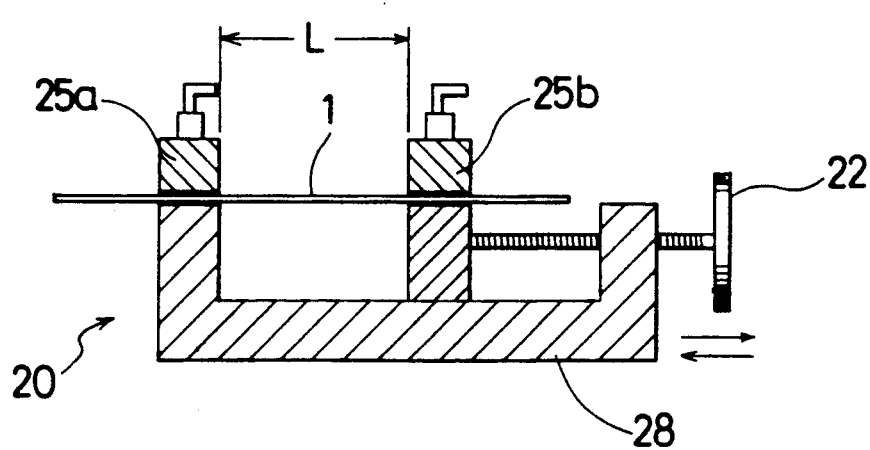
FIG. 3 is a sectional view of a jig for redrawing a crude balloon.

The tapered portions 3a and 3b of the crude balloon is redrawn to reduce their wall thicknesses. FIG. 3 is a sectional view of a jig for stretching the tapered portions 3a and 3b. The jig 20 has two clamps 25a and 25b for holding firmly the crude balloon. The clamp 25b is movably supported on a base 28 and can be moved toward and away from the other clamp 25a by turning a crank 22 on the end of a threaded bar. Any desired part of the crude balloon can be stretched by clamping both sides of that part with the clamps 25a and 25b and then moving the clamp 25b to widen the distance L between the clamps 25a and 25b by turning the crank 22. The wall thickness of the tapered portions 3a and 3b can be made thinner as desired by this redrawing. It is preferable the redrawing rate of the front tapered portion 3a is higher than the redrawing rate of the rear tapered portion 3b. It is preferable to heat the parts of the crude balloon before stretching. The connecting portions 4a and 4b may be stretched together with the tapered portions 3a and 3b as necessary.

After being stretched, the balloon is put into a metal mold (not shown), inflated by pressurized air, heated above the second-order transition temperature of the polymer and then cooled below that temperature while inflated. As the result, the balloon 1 of the present invention is obtained.

Next the balloon catheter of the present invention is described with reference to the embodiment shown in FIGS. 5 and 6.

Figure 5:
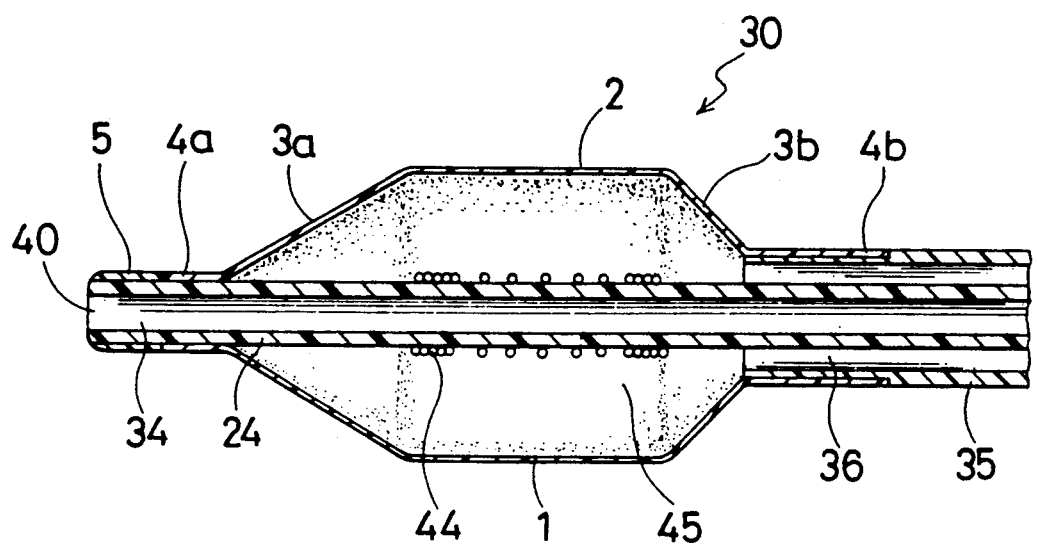
FIG. 5 is a sectional view of the distal end portion of a dilatation catheter as an embodiment of the balloon catheter of the present invention.
Figure 6:
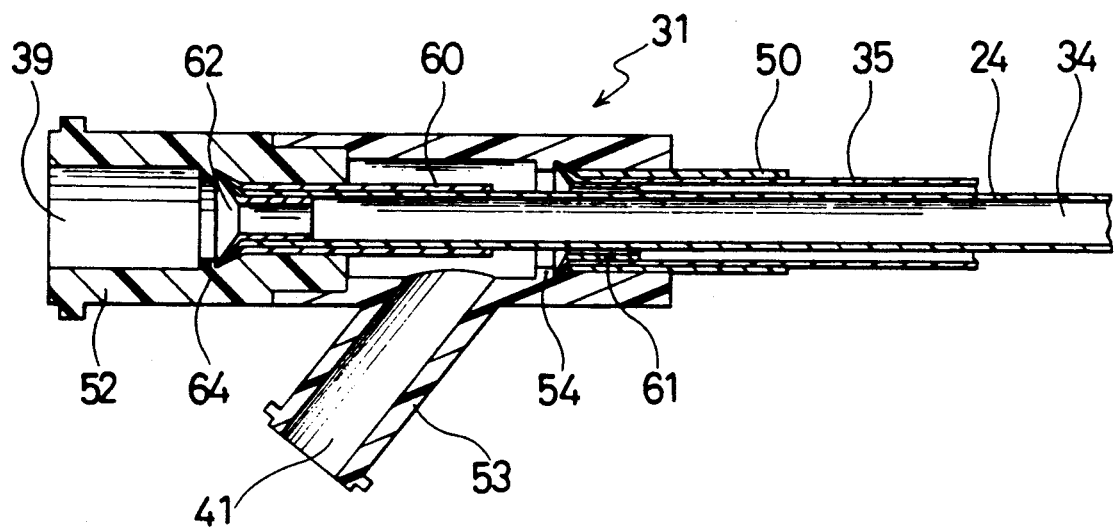
FIG. 6 is a sectional view of the proximal end portion of the same balloon catheter.

FIG. 5 is a sectional view of the distal end portion of the catheter of this embodiment and FIG. 6 is a sectional view of the proximal end portion of the same catheter.

This embodiment is a dilatation catheter equipped with the catheter balloon of the present invention.

The balloon catheter 30 comprises a tubular catheter body comprising an inner tube 24, an outer tube 35 and a branched hub 31 and a balloon 1.

The inner tube 24 has a first lumen 34 with the distal end open. The first lumen 34 is used for passing a guide wire through and in communication with a first bore 39 in the branched hub 31 (described later) serving for a guide wire port. The inner tube 24 has an outside diameter of 0.30 to 2.50 mm, preferably 0.40 to 2.00 mm and an inside diameter of 0.20 to 2.35 mm, preferably 0.25 to 7.70 mm.

For the material for forming the inner tube materials with a certain amount of flexibility are preferable. The materials usable for the inner tube 24 are thermoplastic resins [such as polyolefin (polyethylene, polypropylene, ethylene-propylene copolymer, ethylene-vinyl acetate copolymer, etc.), polyvinyl chloride, polyurethane, polyamide elastomer], silicone rubber and latex rubber. Of the above materials, thermoplastic resins are preferable and olefin resins are more preferable.

The outer tube 35 encases the inner tube 24 and is shorter than the inner tube 24 so as to allow the distal end portion of the inner tube 24 to extend out of its distal end. A second lumen 36 is formed between the inside surface of the outer tube 35 and the outside surface of the inner tube 24. The second lumen 36 is in communication with the inside of the balloon 1 at its distal end. The proximal end of the second lumen 36 is in communication with a second bore 41 in the branched hub 31 serving for an injection port to inject a liquid for expanding the balloon 1.

The outer tube 35 has an outside diameter of 0.50 to 4.30 mm, preferably 0.60 to 4.00 mm and an internal diameter of 0.40 to 3.80 mm, preferably 0.50 to 3.00 mm.

For the material for forming the outer tube 35, materials with a certain amount of flexibility are preferable, The materials usable for the inner tube 24 are thermoplastic resins [such as polyolefin (polyethylene, polypropylene, ethylene-propylene copolymer, ethylene-vinyl acetate copolymer, etc.), polyvinyl chloride, polyurethane, polyamide elastomer], silicone rubber and latex rubber. Of the above materials, thermoplastic resins are preferable and olefin resins are more preferable.

The balloon 1 is foldable and is folded around the inner tube 24 when it is not expanded. It has a hollow cylindrical portion 2 of a substantially uniform diameter so that a stenotic lesion in the blood vessel can be easily dilated. The configuration of the cylindrical portion 2 need not be a right cylinder, but may be a prism. A connecting portion 4b of the balloon 1 is connected with the distal end portion of the outer tube 35 in a liquid-tight manner by means of adhesive bonds or by heating. The other connecting portion 4a is connected with the inner tube 24 near the distal end in the same manner as the connecting portion 4b.

The outside surface of the inner tube 24 from the front end of the connecting portion 4a to the distal end of the inner tube 24 is coated with a soft resin. The rear end of the soft resin layer 5 has substantially the same thickness as that of the connecting portion 4a to fill the step at the front end of the connecting portion 4a. The front end of the soft resin layer 5 is so rounded by cutting off the outside edge that the rounded end of the soft resin layer 5 and that of the inner tube 24 form a continuous curved surface. The soft resin layer 5 end its rounded front end reduce the frictional resistance between the distal end of the balloon catheter (the distal end of the inner tube) and the inside surface of a guide catheter when the balloon catheter is inserted through the guide catheter and that between the distal end of the balloon catheter end the inside surface of the blood vessel when the balloon catheter is advanced in the blood vessel.

The balloon 1 forms a hollow space 45 between its inside surface and the outside surface of the inner tube The rear end of the hollow space 45 is in communication with the second lumen 36. Since the second lumen 36 has a comparatively large sectional area, injection of a liquid into the balloon 1 is easy.

The balloon 1 has tapered portions 3a and 3b formed from the front end of the cylindrical portion 2 to the front connecting portion 4a and from the rear end of the cylindrical portion 2 to the rear connecting portion 4b.

The outside diameter of the cylindrical portion when expanded is 1.00 to 35.00 mm, preferably 1.50 to 3.00 mm; the length of the cylindrical portion when expanded is 3.00 to 80.00 mm, preferably 10.00 to 75.00 mm; and the overall length of the balloon is 5.00 to 20.00 mm, preferably 15.00 to 100.00 mm.

As shown in FIG. 1, the wall thickness A of the cylindrical portion 2 and those indicated by B1 and B2 of the middle parts of the tapered portions 3a and 3b are formed so as to be $B/A \leqq 1.2$, preferably $0.3 \leqq B1/A \leqq 0.9$ or $B1/A \leqq 1.2$ and $B2/A \leqq 1.2$, preferably $0.3 \leqq B1/A \leqq 0.9$ and $0.3 \leqq B2/A \leqq 0.9$. It is preferable that the wall thickness B1 of the front tapered potion 3a is thinner than the wall thickness B2 of the rear tapered potion 3b.

It is also preferable to provide the outside surface of the inner tube 24 with a marker 44 to facilitate the X-ray localization of the cylindrical portion 2. Preferably the marker 44 has substantially the same length as that of the cylindrical portion 2 and is disposed on the outside surface of the inner tube 2 inside the hollow space of the balloon 1 so that its ends ere substantially at the same positions of those of the cylindrical portion 2. For the material of the marker 44, substances impervious or only slightly pervious to radiation such as gold, platinum, tungsten, stainless-steel and their alloy and silver-paladium alloy are preferable. A preferable configuration of the marker 44 is a coil spring, and more preferably a coil spring having closely coiled portions of 1 to 4 mm, preferably 2 to 3 mm at both ends as shown in FIG. 5. A marker of coil spring configuration serves as e reinforcement and prevents bending and collapsing of the inner tube 24 in the blood vessel. The closely coiled portions at the ends of a spring coil make the X-ray localization of the cylindrical portion 2 easier.

Moreover, if a single closely-coiled coil spring is fitted on the outside surface of the inner tube 1, the flexural rigidity of this portion is much more increased.

The cross section of the wire material of the coil spring may be rectangular, circular, square, elliptic or of any other shapes.

The branched hub 31 comprises of a inner-tube hub 52 and an outer-tube hub 53.

The inner-tube hub 52 is attached to the proximal end of the inner tube 24 and provided with the aforementioned first bore 39 communicating with the first lumen 34 and serving for a guide wire port.

The outer-tube hub 52 is attached to the proximal end of the outer tube 35 and provided with the aforementioned second bore 41 communicating with the second lumen 36 and serving for a injection port.

The inner-tube hub 52 and outer-tube hub 53 are connected together into one body.

In the embodiment shown in FIG. 6, a reinforcing tube 50 is fitted over the proximal end portion of the outer tube 35. The reinforcing tube 50 is made of a heat-shrinkable material. It is fitted on the outer tube 35 by forming so as to have an inside diameter a little greater than the outer diameter of the outer tube, putting it on the outer tube, and heating it, for example, by blowing hot air.

The proximal ends of the outer tube 35 is secured to the outer-tube hub 53 by means of a clamping member 61. The clamping member 61 has a cylindrical portion of about the same outside diameter as the inside diameter of the outer tube 35 and about the same inside diameter as the outside diameter of the inner tube 24 and a flared rear end portion of a diameter greater than the outside diameter of the reinforcing tube 50. To secure the outer tube 35 to the outer-tube hub 53, the clamping member 61 is inserted into the rear end of the outer tube 35 and the outer tube 35 is then inserted into the outer-tube hub 53 from the distal end until the flared rear end of the clamping member 61 passes through a projection 54 in the inside surface of the outer-tube hub 53. An adhesive bond may be applied between the inside surface of the outer-tube hub 53 and the outside surface of the reinforcing tube 50.

For the material for the outer-tube hub 53, thermoplastic resins such as polycarbonate, polyamide, polysulfone, Polyacrylate and methacrylate-butylene-styrene-copolymer are preferable.

A reinforcing tube 60 is fitted over the proximal end portion of the inner tube 24. The reinforcing tube 60 is made of e heat-shrinkable material. It is fitted on the inner tube 24 by forming so as to have an inside diameter a little greater than the outside diameter of the inner tube, putting it on the inner tube, and heating it, for example, by blowing hot air.

The proximal ends of the inner tube 24 is secured to the inner-tube hub 52 by means of a clamping member 62. The clamping member 62 has a cylindrical portion of about the same outside diameter as the inside diameter of the inner tube 24 and a flared rear end portion of a diameter greater than the outside diameter of the reinforcing tube 60. To secure the inner tube 24 to the inner-tube hub 52, the clamping member 62 is inserted into the rear end of the inner tube 24 and the inner tube 24 is then inserted into the inner-hub 52 from the distal end until the flared rear end of the clamping member 62 passes through a projection 64 in the inside surface of the inner-hub 52. An adhesive bond may be applied between the inside surface of the inner-tube hub 52 and the outside surface of the reinforcing tube 60.

For the material for the inner-tube 52, thermoplastic resins such as polycarbonate, polyamide, polysulfone, polyacrylate and methacrylate-butylene-styrene-copolymer are preferable.

The inner-tube hub 52 and the outer-tube hub 53 are connected together by fitting the front end portion of the inner-tube hub 52 in the rear end portion of the outer-tube hub 53 as shown in FIG. 6. They can be securely connected by applying an adhesive bond.

Instead of such a branched hub, tubular port members with a bore in their rear end may be connected to the inner and outer tubes respectively in a liquid-tight fashion so that the bore of each port member is in communicate with the corresponding lumen of the balloon.

EXAMPLES

Hereinafter described are examples of the balloon and the balloon catheter of the present invention.

Example 1

A tubular parison was formed of high molecular weight polyethylene terephthalate of the specific viscosity of about 1.1 (UNIPET RT580 from Japan Unipet, molecular weight about 40,000) by extrusion molding. This parison was 0.6 mm in inside diameter, 1.0 mm in outside diameter; and 0.2 mm in wall thickness.

The parison was put in a metal mold as shown in FIG. 2, heated at 85° C., stretched 1.6 times in the direction of its axis, inflated by pressurized air so as to be pressed tightly against the inside surface of the metal mold, and cooled. The drawing ratio of the cylindrical portion by the inflation was about 5 on the inside diameter and about 3 on the outside diameter.

The wall thicknesses of the crude balloon a, b1, and b2 shown in FIG. 4 were 0.013 mm, 0.020 mm and 0.016 mm, respectively. The ratios of the outside diameter of the cylindrical portion to those of the connecting portions f/d and f/e were 2.31 and 2.00. The ratios of the wall thicknesses of the middle parts of the tapered portions to that of the cylindrical portion b1/a and b2/a were 1.54 and 1.23 respectively.

Each tapered portion of this crude balloon was stretched about 3 times in the direction of the axis of the crude balloon using a jig as shown in FIG. 3. The crude balloon was then inflated by pressurized air and heated at 150° C. to heat set. Thus the balloon of the present invention was obtained.

The wall thicknesses of the balloon A, B1, B2, D, E and F shown in FIG. 1 were 0.013 mm, 0.013 mm, 0.010 mm, 0.80 mm, 1.20 mm and 3.00 mm, respectively. The ratios of the outside diameter of the cylindrical portion to those of the connecting portions F/D and F/E were 3.75 and 2.50 respectively. The ratios of the wall thicknesses of the middle parts of the tapered portions to that of the cylindrical portion B1/A and B2/A were 1.00 and 0.77 respectively.

Example 2

A tubular parison was formed of PET copolymer resin (copolymer of polyethylene end terephthalic acid and isophthalic acid) of the specific viscosity of about 0.8 (UNIPET RN165 from Japan Unipet, molecular weight about 30,000) by extrusion molding. This parison had the inside diameter of 0.40 mm, the outside diameter of 0.72 mm, and the wall thickness of 0.16 mm.

A crude balloon was formed from this parison by heating it at b 85° C., stretching it in the direction of its axis and inflated it in the same manner as in example 1. The drawing ratio in the direction of the axis was 2.5. The drawing ratio of the cylindrical portion by the inflation was about 4.9 on the inside diameter and about 2.8 on the outside diameter.

The wall thicknesses of the crude balloon a, b1, and b2 shown in FIG. 4 were 0.011 mm, 0.016 mm and 0.014 mm, respectively. The ratios of the outside diameter of the cylindrical portion to those of the connecting portions f/d and f/e were 2.00 and 1.67 respectively. The ratios of the wall thicknesses of the middle parts of the tapered portions to that of the cylindrical portion b1/a and b2/a were 1.45 and 1.27 respectively.

Each tapered portion of this crude balloon was stretched about 3 times (but, the drawing rate of the front tapered portion is higher than the drawing rate of the rear tapered portion) in the direction of the axis of the crude balloon while heating the tapered portion and connecting portion at about 100° C. by hot air. This crude balloon was inflated again and heated at 150° C.

The wall thicknesses of the balloon A, B1, and B2 shown in FIG. 1 were 0.011 mm, 0.009 mm and 0.010 mm. The ratios of the outside diameter of the cylindrical portion to those of the connecting portions F/D and F/E were 2.50 and 1.67 respectively. The ratios of the wall thicknesses of the middle parts of tapered portions to that of the cylindrical portion B1/A and B2/A were 0.82 and 0.91 respectively.

Example 3

A tubular parison was formed of PET copolymer resin of the specific viscosity of about 0.8 (UNIPET RN165 from Japan Unipet, molecular weight about 30,000) by extrusion molding. This parison had the inside diameter of 0.6 mm, the outside diameter of 1.082 mm and the wall thickness of 0.24 mm.

A crude balloon was formed from this parison by heating it at 90° C. stretching it in the direction of its axis and inflating it in the same manner as in example 1. The drawing ratio in the direction of the axis was 2.5. The drawing ratio of the cylindrical portion by the inflation was about 5.8 on the inside diameter and about 3.2 on the outside diameter.

The wall thicknesses of the crude balloon a, b1, and b2 shown in FIG. 4 were 0.016 mm, 0.028 mm and 0.023 mm, respectively. The ratios of the outside diameter of the cylindrical portion to those of the connecting portions f/d end f/e were both 2.92 respectively. The ratios of the wall thicknesses of the middle parts of the tapered portions to that of the cylindrical portion b1/a and b2/a were 1.75 and 1.44 respectively.

Each tapered portion of this crude balloon was stretched about 3 times (but, the drawing rate of the front tapered portion is higher than the drawing rate of the rear tapered portion) in the direction of the axis of the balloon while heating the tapered portion and connecting portion at about 100° C. by hot air. This crude balloon was then inflated again and heated at 90° C.

The wall thicknesses of the balloon A, B1, and B2 shown in FIG. 1 were 0.015 mm, 0.017 mm and 0.018 mm. The ratios of the outside diameter of the cylindrical portion to those of the connecting portions F/D and F/E were both 2.92 respectively. The ratios of the wall thicknesses of the middle parts of the tapered portions to that of the cylindrical portion B1/A and B2/A were 1.13 and 1.20 respectively.

Each tapered portion of this balloon was again stretched about 1.2 tames in the direction of the axis of the balloon while heating the tapered portion and connecting portion at about 100° C. by hot air. The balloon was then inflated and heated at 150° C. again. Thus the balloon of the present invention was obtained.

The well thicknesses A, B1, and B2 of the balloon shown in FIG. 1 were 0.015 mm, 0.010 mm and 0.013 mm, respectively. The ratios of the outside diameter of the cylindrical portion to those of the connecting portions F/D. and F/E were 4.83 and 2.92 respectively. The ratios of the wall thicknesses of the middle parts of the tapered portions to that of the cylindrical portion B1/A and B2/A were 0.67 and 0,87 respectively.

Example 4

A double-layer tube with the inside diameter of 0.95 mm, the outside diameter of 1.17 mm and the length of 1,300 mm was formed of polyethylene and EVA copolymer and used as the outer tube. An inner layer of the tube was formed of polyethylene. An outer layer of the tube was formed of EVA copolymer. A tube with the inside diameter of 0.5 to 0.55 mm, the outside diameter of 0.70 mm and the length of 1,350 mm was formed of polyethylene and used as the outer tube.

A catheter of the construction as shown in FIGS. 5 and 6 was made using this tubular catheter body and the balloon of example 1.

Example 5

A balloon catheter was made using the catheter body obtained in example 4 and the balloon of example 2.

Example 6

A balloon catheter was made using the catheter body obtained in example 4 and the balloon of example 3.

Comparative Example 1

The crude balloon before restretching in example 1 was used as comparative example 1. The wall thicknesses of the crude balloon a, b1, and b2 shown in FIG. 4 were 0.013 mm, 0.020 mm and 0.016 mm, respectively. The ratios of the outside diameter of the cylindrical portion to those of the connecting portions f/d and f/e were 2.31 and 2.00 respectively, and those of the wall thicknesses of the middle parts of the tapered portions to that of the cylindrical portion b1/a and b2/a were 1.54 and 1.23 respectively.

Comparative Example 2

A balloon catheter was made using the catheter body obtained in example 4 and the crude balloon of comparative example 1.

Comparative Example 3

The crude balloon before restretching In example 2 was used as comparative example 3. The wall thicknesses of the crude balloon a, b1, and b2 shown in FIG. 4 were 0.016 mm, 0.028 mm and 0.023 mm, respectively. The ratios of the outside diameter of the cylindrical portion to those of the connecting portions f/d and f/e were both 2.92. The ratios of the wall thicknesses of the middle parts of the tapered portions to that of the cylindrical portion b1/a and b2/a were 1.75 and 1.44 respectively.

Comparative Example 4

The crude balloon before restretching in example 3 was used as comparative example 4. The wall thicknesses of the crude balloon a, b1, and b2 shown in FIG. 4 were 0.016 mm, 0.028 mm and 0.023 mm, respectively. The ratios of the outside diameter of the cylindrical portion to those of the connecting portions f/d and f/e were both 2.92. The ratios of the wall thicknesses of the middle parts of the tapered portions to that of the cylindrical portion b1/a and b2/a were 1.75 and 1.44 respectively.

Comparative Example 5

A balloon catheter was made using the catheter body obtained in example 4 and the crude balloon of comparative example 3.

Comparative Example 6

A balloon catheter was made using the catheter body obtained in example 4 and the crude balloon of comparative example 4.

Tests

A syringe was attached to the injection port of the balloon catheter of example 4. The balloon was inflated by injecting a liquid into the second lumen and then folded by sucking out the liquid.

The same tests were conducted on the balloon catheters of examples 5 and 6 and comparative examples 2, 5 and 6.

Figure 7:
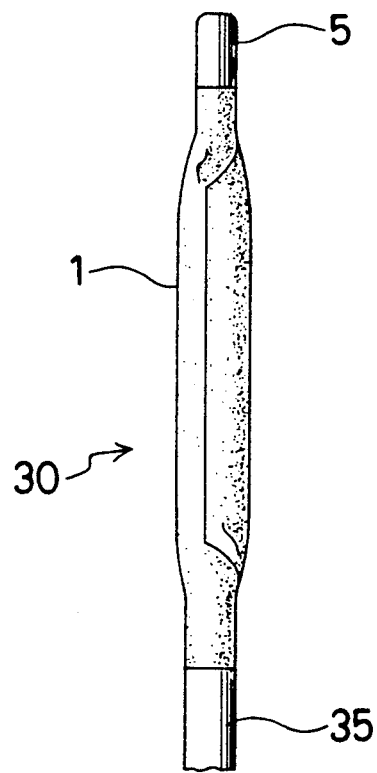
FIG. 7 is a diagrammatic view of the balloon of the present invention attached to a catheter body and folded around the catheter body.
Figure 8:
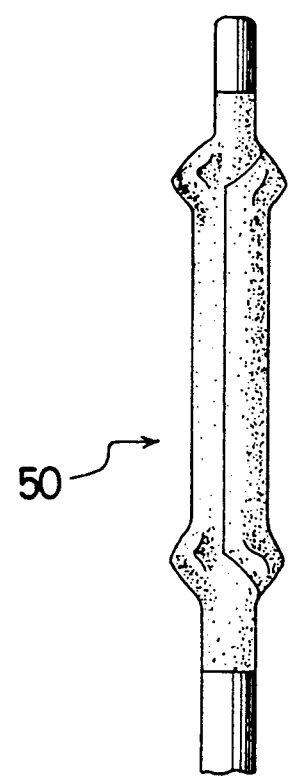
FIG. 8 is a diagrammatic view of a conventional balloon attached to a catheter body and folded around the catheter body.

The protruberation and angulateness of the wrinkles caused by the tapered portions were smaller and softer in the balloons of the catheters of examples 4, 5 and 6 than in that of the catheters of comparative examples 2, 5 and 6 as shown in FIGS. 7 and 8.

As described above, the catheter balloon of the present invention is made of a polymer, comprises a cylindrical portion of a substantially uniform diameter, tapered portions at the front and rear of the cylindrical portion end tubular connecting portions at the front and rear of the tapered portions, and is characterized in that the wall thicknesses (B) of the substantially middle parts of the tapered portions are equal to or smaller than 1.2 times the wall thickness (A) of the cylindrical portion (B/A 23 1.2). Since the walls of the tapered portions are thin, the protruberation and angularness of wrinkles caused by the tapered portions when the balloon is folded are smaller and softer than those of conventional balloons. Therefore, the balloon of the present invention, when used in a dilatation catheter, can be inserted easily in the blood vessel without hurting the inside surface of the blood vessel and thereby causing new thrombosis or stenosis.

The balloon catheter of the present invention comprises a tubular catheter body and a balloon which is made of a polymer, comprises a cylindrical portion of a substantially uniform diameter, tapered portions at the front and rear of the cylindrical portion and connecting portions at the front and rear of the tapered portions, and is characterized in that the wall thicknesses (B) of the substantially middle parts of the tapered portions are equal to or smaller than 1.2 times the wall thickness (A) of the cylindrical portion (B/A≦1.2). Since the protruberation and angularness of wrinkles when the balloon is folded are smaller and softer, the balloon catheter of the present invention can be inserted easily in the blood vessel without hurting the inside surface of the blood vessel and thereby causing new thrombosis or stenosis.

The method of the present invention for manufacturing the catheter balloon of the present invention comprising, forming a parison out of a drawable polymer, heating the parison et a temperature in the range from the second-order transition temperature to the first-order transition temperature of the polymer used, and then stretching it in the direction of its axis and then inflating it radially while heated, and then cooling the stretched and inflated parison below the second-order transition temperature of the polymer, and then deflating it, a crude balloon thus formed having a cylindrical portion of a substantially uniform desired diameter and desired wall thickness, tapered portions of the wall thicknesses thicker than desired thicknesses at the front and rear of the cylindrical portion and connecting portions at the front and the rear of the tapered portions, and then redrawing the tapered portions of the crude balloon to reduce their wall thicknesses to desired thicknesses by stretching the tapered portions in the direction of the axis of the crude balloon, and then inflating the crude balloon, and then heating it above the second-order transition temperature of the polymer, and then cooling it. By this method, the catheter balloon of the present invention can be manufactured easily at a low cost.

What is claimed is:

1. In a catheter balloon made of a polymer and comprising a cylindrical portion of a substantially uniform diameter, tapered portions at front and rear portions of the cylindrical portion, and connecting portions at the front and rear of the tapered portions, the cylindrical and tapered portions having a wall thickness, the improvement wherein:

the balloon, including the tapered portions and the cylindrical portion, is made by biaxially drawing;
the tapered portions are redrawn;

substantially middle parts of the tapered portions have wall thicknesses (B) which are equal to or greater than 0.3 times the wall thickness (A) of said cylindrical portion, and the wall thicknesses (B) of the substantially middle parts of the tapered portions are equal to or smaller than 0.9 times the wall thickness (A) of said cylindrical portion; and the wall thickness of the front tapered portion is thinner than the wall thickness of a rear tapered portion and said cylindrical portion.

2. A catheter balloon as claimed in claim 3 in which the polymer is a mixture of polyethylene terephthalate and a polyolefin selected from the group consisting of polyethylene and polypropylene.

3. (Amended) A catheter balloon as claimed in claim 1, in which said polymer is selected from the group consisting of (a) polyethylene terephthalate, (b) a mixture of polyethylene terephthalate and a polyester other than polyethylene terephthalate, (c) a mixture Of polyethylene terephthalate and a polyolefin and (d) a polyethylene terephthalate copolymer.

4. In a balloon catheter comprising a tubular catheter body coupled to a balloon and including means for inflating the balloon, and wherein the balloon is made of a polymer, the balloon comprising a cylindrical portion of a substantially uniform diameter, tapered portions at front and rear portions of the cylindrical portion, and connecting portions at the front and rear of the tapered portions, the cylindrical and tapered portions having a wall thickness, the improvement wherein:

the balloon, including the tapered portions and the cylindrical portion, is made by biaxially drawing:

the tapered portions are redrawn;

substantially middle parts of the tapered portions have wall thicknesses which are equal to or greater than 0.3 times the wall thickness (A) of said cylindrical portion, and the wall thicknesses (B) of the substantially middle parts of the tapered portions are equal to or smaller than 0.9 times the wall thickness (A) of said cylindrical portion; and the wall thickness of the front tapered portion is thinner than the wall thickness of a rear tapered portion and the cylindrical portion.

5. A balloon catheter as claimed in claim 4, in which said polymer is selected from the group consisting of (a) polyethylene terephthalate, (b) a mixture of polyethylene terephthalate and a polyester other than polyethylene terephthalate, (c) a mixture of polyethylene terephthalate and a polyolefin and (d) a polyethylene terephthalate copolymer.

6. A balloon catheter as claimed in claim 5 in which the polymer is a mixture of polyethylene terephthalate and a polyolefin selected from the group consisting of polyethylene and polypropylene.

* * * * *

UNITED STATES PATENT AND TRADEMARK OFFICE
CERTIFICATE OF CORRECTION

PATENT NO. : 5,334,146
DATED : August 2, 1994
INVENTOR(S) : H. OZASA

It is certified that error appears in the above-indentified patent and that said Letters Patent is hereby corrected as shown below:

Column 2, line 59, insert --is-- after "invention";

Column 2, line 63, after "made" insert --of--;

Column 4, line 48, delete "e" and insert --a--;

Column 4, line 53, "Combined" should be --combined--;

Column 11, line 20, change "In" to --in--; and

Column 12, line 7, delete "(B/A 23 1.2)" and insert --(B/A <_ 1.2)--.

Signed and Sealed this

Twenty-sixth Day of November 1996

Attest:

BRUCE LEHMAN

Attesting Officer     Commissioner of Patents and Trademarks